(12) United States Patent
Nifantiev et al.

(10) Patent No.: US 6,949,581 B2
(45) Date of Patent: Sep. 27, 2005

(54) WATER-SOLUBLE MONO-PEGYLATED TETRAPYRROLE DERIVATIVES FOR PHOTODYNAMIC THERAPY AND METHOD OF PRODUCTION

(75) Inventors: Nikolay E. Nifantiev, Moscow (RU); Dmitri V. Yashunsky, Moscow (RU)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 10/394,877

(22) Filed: Mar. 21, 2003

(65) Prior Publication Data

US 2004/0186285 A1 Sep. 23, 2004

(51) Int. Cl.[7] .................... C07D 487/22; A61K 31/409; A61P 35/00
(52) U.S. Cl. ....................... 514/410; 540/145
(58) Field of Search ........................... 540/145; 514/410

(56) References Cited

U.S. PATENT DOCUMENTS

| | | | |
|---|---|---|---|
| 5,330,741 A | 7/1994 | Smith et al. |
| 5,378,835 A | 1/1995 | Nakazato |
| 5,622,685 A | 4/1997 | Sinn et al. |
| 6,147,207 A | 11/2000 | Sinn et al. |
| 2003/0023081 A1 | 1/2003 | Nifantiev et al. |

FOREIGN PATENT DOCUMENTS

| | | |
|---|---|---|
| RU | 2144538 | 1/2000 |
| WO | WO 01/66550 A2 | 9/2001 |

OTHER PUBLICATIONS

Sternberg et al, "Porphyrin-based Photosensitizers for Use in Photodynamic Therapy", Tetrahedron 1998; 54:4151–4202.

Bonnett, "Photodynamic Therapy in Historical Perspective", Rev. Contemp. Pharmacother. 1999; 10:1–17.

Leach et al, "Effectiveness of a Lysyl Chlorin p6/Chlorin p6 Mixture in Photodynamic Therapy of the Subcutaneous 9L Glioma in the Rat", Cancer Research Mar. 1, 1992;52:1235–1239.

Lotjonen et al, "An Improved Method for the Preparation of (10R)– and (10S)–Pheophytins a and b", Synthesis 1983;705–708.

Hynninen et al, "Preparation of Phorbin Derivatives from Chlorophyll Mixture Utilizing the Principle of Selective Hydrolysis", Synthesis 1980:539–541.

Lotjonen et al, "A Convenient Method for the Preparation of Chlorin e6 and Rhodin g7 Trimethyl Esters", Synthesis 1980:541–543.

Primary Examiner—James O. Wilson
Assistant Examiner—Kahsay Habte
(74) Attorney, Agent, or Firm—Bolesh J. Skutnik; B J Associates

(57) ABSTRACT

Water-soluble mono-PEGylated tetrapyrrole derivatives are disclosed, having a formula given by formula 1, 2, or 3 in the specification. A method to produce the above water-soluble mono-PEGylated compounds is also disclosed, comprising an interaction of a tetrapyrrole with an aminopolyethylene glycol containing a functionalized terminal fragment, as well as their use as photosensitizers in photodynamic therapy.

7 Claims, No Drawings

WATER-SOLUBLE MONO-PEGYLATED TETRAPYRROLE DERIVATIVES FOR PHOTODYNAMIC THERAPY AND METHOD OF PRODUCTION

BACKGROUND OF THE INVENTION

1. Field of the Invention

The invention relates to the chemistry of biologically active compounds, namely, to a new method to prepare water-soluble mono-PEGylated tetrapyrrole derivatives, particularly chlorin, bacteriochlorin, pheophorbide and bacteriopheophorbide derivatives of types 1, 2 and 3. The compounds of the present invention can be used as photosensitizers for the photodynamic therapy of cancer, infections and other diseases as well as for light irradiation treatments in other cases.

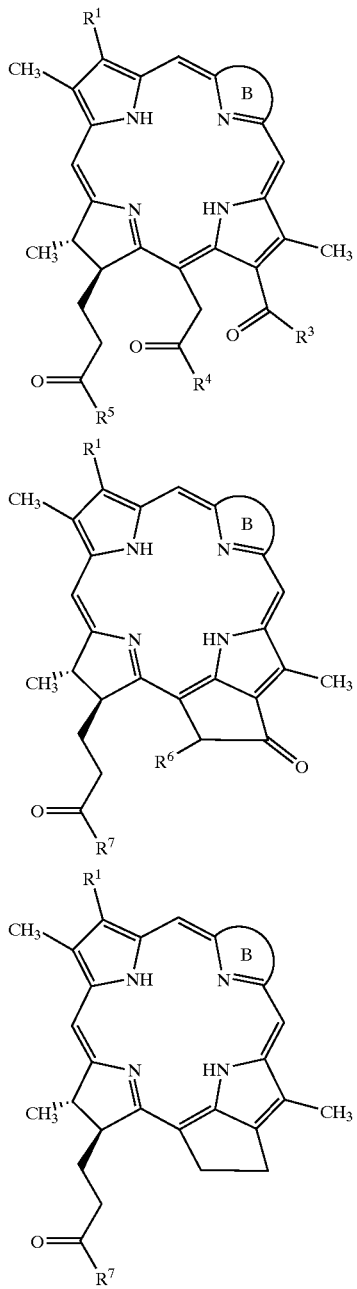

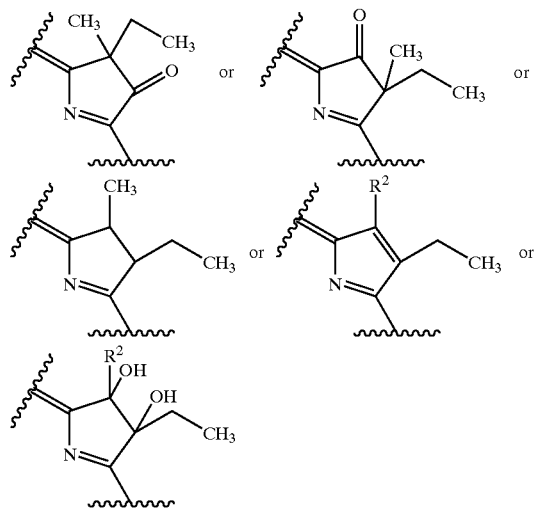

Wherein B is a ring having the structure:

Wherein:
$R^1$=—CH=CH$_2$, —CH(OAlk)CH$_3$, —CHO, —C(O)CH$_3$, —CH$_2$CH$_3$, —CH(Alk)CH(COAlk)$_2$, —CH$_2$CH(COAlk)$_2$, —CH(Alk)CH$_2$COAlk, —CH(Alk)CH$_2$CH(OH)CH$_3$, and —CH$_2$CH$_2$CH(OH)CH$_3$;

$R^2$=—CH$_3$, —CHO, —CH(OH)Alk, —CH=CHAlk, CH$_2$OH, and CH$_2$OAlk;

$R^3$=—OH, —OAlk, —NH-Alk, —NR$^8$—R$^9$—R$^{10}$, —NH(CH$_2$)$_m$—R$^{11}$—R$^9$—R$^{10}$;

$R^4$=—OH, —OAlk, —NH-Alk, —NR$^8$—R$^9$—R$^{10}$, —NH(CH$_2$)$_m$—R$^{11}$—R$^9$—R$^{10}$;

$R^5$=OH, —OAlk, —NH-Alk, —NR$^8$—R$^9$—R$^{10}$, —NH(CH$_2$)$_m$—R$^{11}$—R$^9$—R$^{10}$;

$R^6$=H and —COOAlk;

$R^7$=NR$^8$—R$^9$—R$^{10}$, —NH(CH$_2$)$_m$—R$^{11}$—R$^9$—R$^{10}$;

$R^8$=H and -Alk;

$R^9$=—(CH$_2$CH$_2$O)$_n$CH$_2$CH$_2$—;

$R^{10}$=—OH, —OAlk, —NH$_2$, —NHAlk, —NHAcyl, —NAcyl$_2$, —NR$^{12}$R$^{13}$, —COR$^{14}$, —OCH$_2$COR$^{14}$;

$R^{11}$=—CH$_2$CONR$^8$—, —NHCOO—;

$R^{12}$=H and -Alk;

$R^{13}$=H and -Alk; and $R^{14}$=—OH, —OAlk, —NR$^{12}$R$^{13}$;

Wherein:
m=2–12;
n=8–500; and
Alk=an alkyl substituent.

2. Information Disclosure Statement

Photodynamic therapy (PDT) is one of the most promising new techniques now being explored for use in a variety of medical applications, and particularly is a well-recognized treatment for the destruction of tumors (E. D. Sternberg et al, "Porphyrin based photosensitizers for Use in Photodynamic Therapy," Tetrahedron 54 (1998) 4151–4202).

Criteria are provided which a compound has to meet to at least some extent in order to be successfully used in PDT. (R. Bonnett, "Photodynamic Therapy in Historical Perspective", Rev. Contemp. Pharmacother. 1999, 10, 1–17) They are the following:

1. high quantum yield of reactive species, such as singlet —oxygen or radicals;

2. relatively low toxicity to the subject;
3. capability of being activated by radiation with a high wavelength (preferably in the red or near infra-red region of the spectrum), which is able to penetrate more deeply into the tissues as compared to radiation with a shorter wavelength;
4. selective accumulation by cells that are responsible for a given pathological condition and rapid elimination from the tissues that are not affected by the pathological condition;
5. potential for being conjugated to macromolecular carries, albeit maintaining the characteristics of photosensitization efficiency, and
6. solubility in suitable solvents to facilitate administration to a patient and physiological uptake and transport within the patient's body.

Tetrapyrroles are compounds widely used in PDT. A major problem in the pharmaceutical application of tetrapyrroles is their low solubility in physiological solutions. This renders it difficult to prepare effective pharmaceutical grade injectable solutions for PDT and other applications.

Methods to prepare water soluble tetrapyrrole derivatives for PDT are known in the art. U.S. Pat. No. 5,330,741 by Smith et al discloses a method to prepare trisodium lysylchlorin $p_6$ involving the reaction between purpurin 18 methyl ester, resulting from methyl pheophorbide a transformation, and aqueous lysine in methylene chloride in the presence of pyridine. The mixture is stirred at room temperature for 12 hours, followed by the removal of the solvents in a high vacuum. The so prepared crude product is purified by reversed phase high performance liquid chromatography (HPLC) and subsequently lyophilized. To prepare an injectable solution for the PDT of cancer, the preparation is first dissolved in phosphate buffer solution and then 0.1 N sodium hydroxide is added. The pH value of the solution is adjusted to pH 7.35 using 0.1 N HCl followed by sterility filtration through a microporous filter. Drawbacks of the above-mentioned method include a lack of reproducibility and difficulty in the work-up and utilization of toxic reagents, which make it hardly appropriate for pharmaceutical manufacturing. Additionally, the prepared water soluble product of interest is stable in an aqueous solution for only 24 hours at 4° C. in the dark, and in solid form for up to 4 months at 4° C. in the dark [M. W. Leach, R. J. Higgins, J. E. Boggan, S.-J. Lee, S. Autry, K. M. Smith, Effectiveness of a Lysylchlorin $p_6$/Chlorin $p_6$ mixture in Photodynamic Therapy of the Subcutaneous 9L Glioma in the Rat. Cancer Res., 1992, 52, 1235–1239; U.S. Pat. No. 5,330,741].

There is a method to prepare a water-soluble sodium salt of pheophorbide a (4), described in U.S. Pat. No. 5,378,835 by Nakazato. According to this invention, pheophorbide a (5) is dissolved in diethyl ether, and a very diluted solution of alkali in n-propanol, iso-propanol or in their mixture is added dropwise and very slowly to the solution. The reaction is maintained up to the complete precipitation of pheophorbide a salt (4), which is separated by centrifugation and dried in vacuo. Then the product is dissolved in water resulting in a solution with concentration 0.5% and pH 9.2–9.5 that is then diluted with a phosphate buffer with pH 7.4–7.8. The drawback of the method described by Nakazato is the fact that a concentrated (>1%) injectable pheophorbide a solution in water cannot be generated by this technique. Additionally, the authors of the present invention observed the chemical instability of such salts when stored dry, and their inability to completely dissolve in water after having been stored in the dry state.

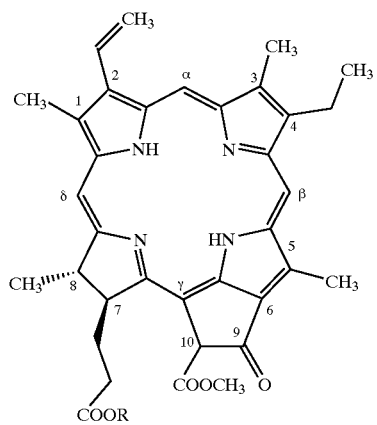

(4) R = Na
(5) R = H

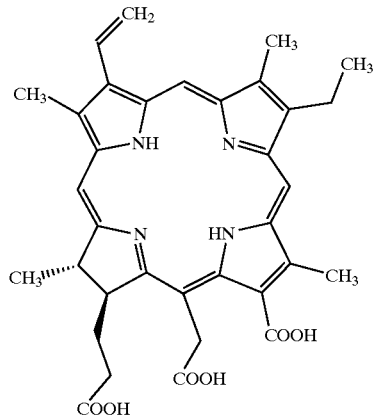

(6)

There is a method disclosed in Russian Patent No. RU2144538 by G. V. Ponomarev et al to prepare water-soluble complexes of chlorin $e_6$ (6) with spacious organic amines including N-methyl-D-glucosamine by a multi-step straightforward sequence of chemical reactions including preparation of chlorophyll a from Spirulina Platensis cyanobacteria biomass, further conversion into chlorin $e_6$ according to standard procedures [S. Lötjönen, P. H. Hynninen, An improved method for the preparation of (10R)-and (10S)-pheophytins a and b. Synthesis. 1983, 705–708; P. H. Hynninen, S. Lötjönen, Preparation of phorbin derivatives from chlorophyll mixture utilizing the principle of selective hydrolysis. Synthesis. 1980, 539–541; S. Lötjönen, P. H. Hynninen, A convenient method for the preparation of wet chlorin $e_6$ and rhodin $g_7$ trimethyl esters. Synthesis, 1980, 541–543] with an overall yield exceeding 50% after precipitation of chlorin $e_6$ (6) by way of stepwise addition of water to its acetone solution, followed by separation by centrifugation and 3-fold washing with water and subsequent treatment of wet chlorin $e_6$ with water solution of 2 g-eq. spacious organic amine. Unfortunately the samples of water soluble salts of chlorin $e_6$ prepared according to the above method contain a variety of impurities of non-tetrapyrrole and tetrapyrrole types which can't be separated from the target chlorin $e_6$ product using conventional procedures.

There is a method to prepare highly pure pharmaceutical-grade water-soluble tetrapyrrole derivatives comprising the steps of: one or two step direct acidic alcoholysis of biological raw material giving crystalline alkyl pheophorbide, conversion of the obtained alkyl pheophorbide into pheophorbide, and reacting of the latter with a hydrophilic organic amine in a medium selected from a group consisting of water and an aqueous organic solution (U.S. patent application Ser. No. 10/151,764 by Nifantiev et al). The hydrophilic organic amine is selected from the group consisting of N-methyl-D-glucamine, aminoalkyl glycosides, tris(hydroxymethyl)aminomethane ("TRIS") and derivatives thereof, aminoacids and oligopeptides.

Obtaining water-soluble compounds for pharmaceutical applications by means of so-called PEGylation, that is by direct or indirect (via linker) attachment of polyethylene glycol chains (PEG), is known in the art. PEG is non-toxic, increases the water solubility of therapeutic molecules, and alters the biodistribution, which can result in a favorable pharmacokinetic profile (International Application No. WO 01/66550 by Bradley et al).

Water-soluble PEGylated compounds for PDT are disclosed in U.S. Pat. No. 5,622,685 by Sinn et al, wherein said compounds have at least two phenolic hydroxyl and/or amino groups, at least one aliphatic amino group, or at least one phenolic hydroxyl and/or amino group and at least one aliphatic amino group, and these groups are substituted with polyethylene glycol chains, whose degree of polymerization n is 5 to 250 and whose terminal hydroxyl group is substituted by $C_1$–$C_{12}$ alkyl ester or ether, each substance being substituted by at least two such polyethylene glycol chains. U.S. Pat. No. 5,622,685 also describes compounds containing PEG chains attached via linker wherein the polyethylene glycol chains are attached via biologically non-hydrolyzable or poorly hydrolyzable linkers.

The closest analogue to the present invention is the method disclosed in U.S. Pat. No. 6,147,207 by Sinn et al. entitled "Method for producing chlorins and bacteriochlorins containing polyether". The method includes the bonding of a polyether to a porphyrin and conversion of the porphyrin containing polyether by means of a reducing agent. In the preferred embodiment of the invention the polyether is a polyethylene glycol (PEG). The key disadvantage of the method is that only a very limited number of compounds can be obtained due to the chemistry of the process. Also, the application (as well as other applications by Sinn et al.) discloses bis-, tris or tetra-PEGylated compounds, but not mono-PEGylated compounds. In practice it is possible to get only a complex mixture of isomers and oligomers of PEG-residue containing compounds. This fact makes reliable quantitative analysis and quality control, which are mandatory for the preparation of pharmaceutical products, practically impossible. Moreover, U.S. Pat. No. 6,147,207 discloses the preparation of products which bear PEG-chains which could be terminated only with OH and OMe groups, thus limiting the practical use of the obtained compounds.

Thus there is a need to provide new water-soluble mono-PEGylated tetrapyrrole derivatives for photodynamic therapy and to provide an easy and efficient method to produce such water-soluble mono-PEGylated compounds. The present invention addresses these needs.

OBJECTIVES AND BRIEF SUMMARY OF THE INVENTION

It is an object of the present invention to provide an improved photosensitizer for use in photodynamic therapy (PDT) of cancer, infections and other diseases.

It is another object of the present invention to provide water-soluble tetrapyrrole derivatives, that can be used as photosensitizers in PDT and are stable for extended periods of time.

It is yet another object of the present invention to provide a reproducible and efficient method for manufacturing improved water-soluble tetrapyrrole derivatives for use in PDT.

Briefly stated, provided herein is a method of producing water-soluble mono-PEGylated tetrapyrrole derivatives (1)–(3), comprising an interaction of one of compounds (7)–(10) with an aminopolyethylene glycol containing a functionalized terminal fragment. Compounds (7)–(10) are provided below:

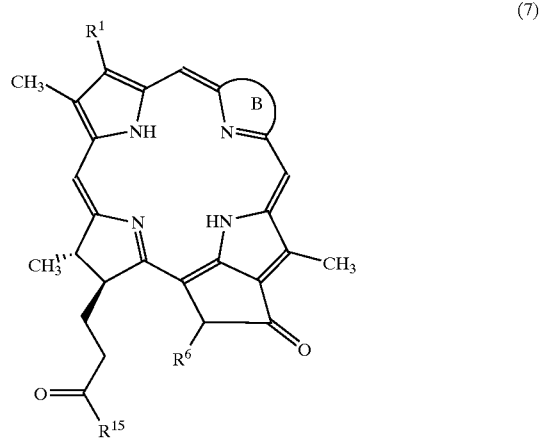

(7)

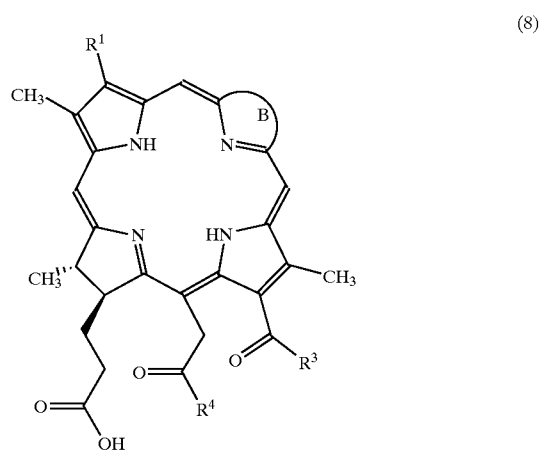

(8)

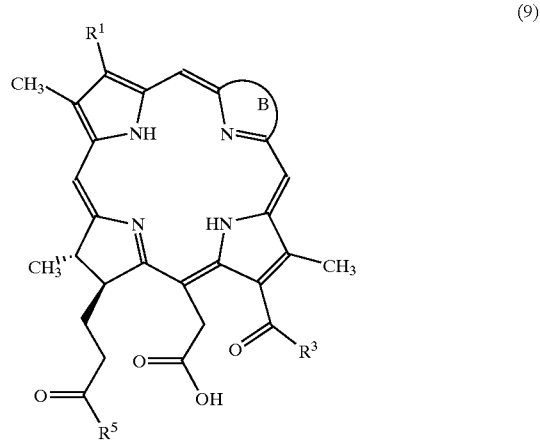

(9)

-continued

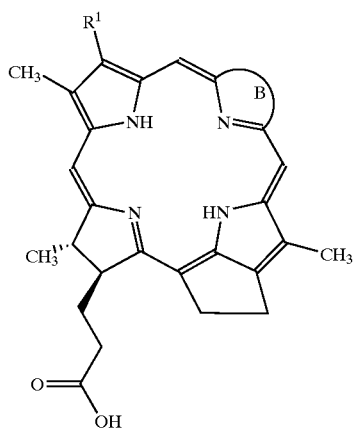
(10)

Wherein B is a ring having the structure:

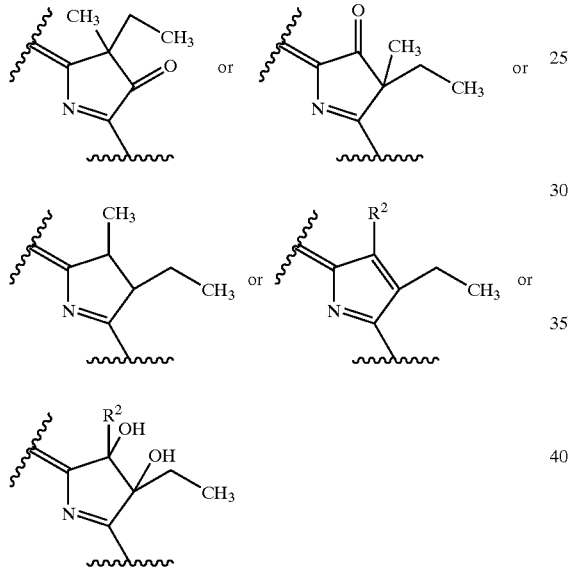

Wherein:
R$^1$=—CH=CH$_2$, —CH(OAlk)CH$_3$, —CHO, —C(O)CH$_3$, —CH$_2$CH$_3$, —CH(Alk)CH(COAlk)$_2$, —CH$_2$CH(COAlk)$_2$, —CH(Alk)CH$_2$COAlk, —CH(Alk)CH$_2$CH(OH)CH$_3$, and —CH$_2$CH$_2$CH(OH)CH$_3$;
R$^2$=—CH$_3$, —CHO, —CH(OH)Alk, —CH=CHAlk, CH$_2$OH, and CH$_2$OAlk;
R$^3$=—OH, —OAlk, —NH-Alk;
R$^4$=—OH, —OAlk, —NH-Alk;
R$^5$=—OH, —OAlk, —NH-Alk;
R$^6$=H and —COOAlk;
R$^{15}$=OH, —NH(CH$_2$)$_m$—R$^{16}$;
R$^{16}$=—COOH, —NH$_2$;
Wherein:
m=2–12; and
Alk=an alkyl substituent.

The functionalized terminal fragment (indicated as R$^{10}$ (see formulae (1)–(3))) is preferably selected from the group comprising:
R$^{10}$=—OH, —OAlk, —NH$_2$, —NHAlk, —NHAcyl, —NAcyl$_2$, —NR$^{12}$R$^{13}$, —COR$^{14}$, —OCH$_2$COR$^{14}$, wherein R$^{12}$=H and -Alk;
R$^{13}$=H and -Alk;
R$^{14}$=—OH, —OAlk, —NR$^{12}$R$^{13}$; and
Alk=an alkyl substituent. OAlk is preferably OMe. The aminopolyethylene glycol containing a functionalized terminal fragment has a molecular weight of 500–30000.

Also provided is a water-soluble mono-PEGylated tetrapyrrole derivative, selected from the group, comprising:

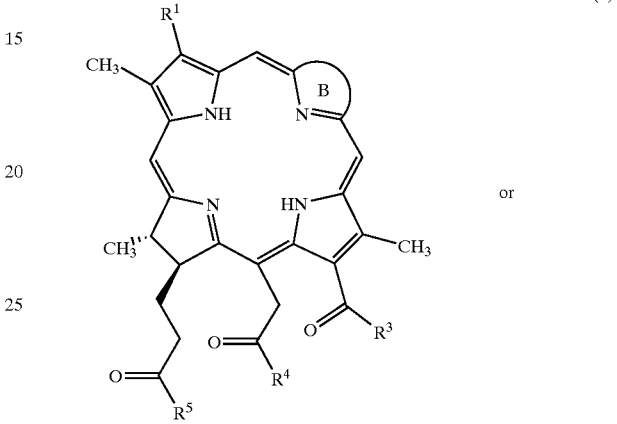
(1)
or

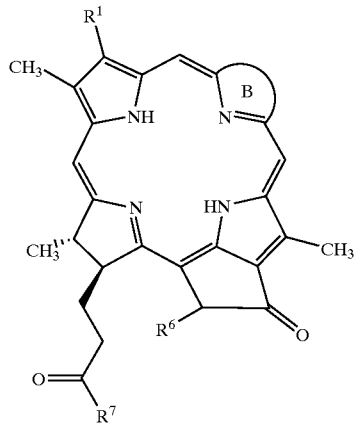
(2)
or

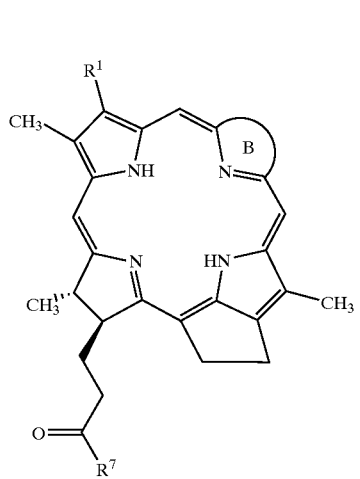
(3)

Wherein B is a ring having the structure:

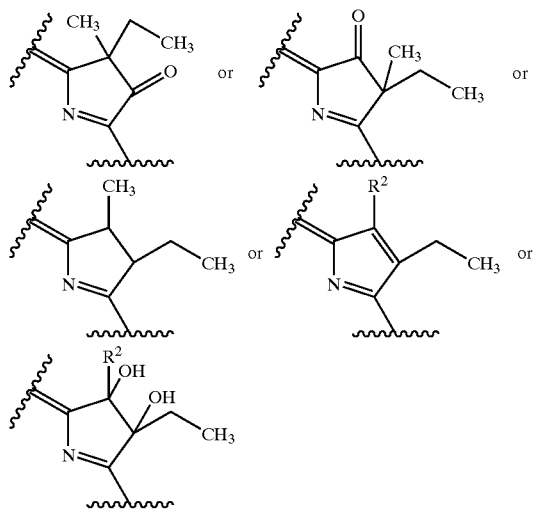

Wherein:

$R^1$=—CH=CH$_2$, —CH(OAlk)CH$_3$, —CHO, —C(O)CH$_3$, —CH$_2$CH$_3$, —CH(Alk)CH(COAlk)$_2$, —CH$_2$CH(COAlk)$_2$, —CH(Alk)CH$_2$COAlk, —CH(Alk)CH$_2$CH(OH)CH$_3$, and —CH$_2$CH$_2$CH(OH)CH$_3$;

$R^2$=—CH$_3$, —CHO, —CH(OH)Alk, —CH=CHAlk, CH$_2$OH, and CH$_2$OAlk;

$R^3$=—OH, —OAlk, —NH-Alk, NR$^8$—R$^9$—R$^{10}$, —NH(CH$_2$)$_m$—R$^{11}$—R$^9$—R$^{10}$;

$R^4$=—OH, —OAlk, —NH-Alk, NR$^8$—R$^9$—R$^{10}$, —NH(CH$_2$)$_m$—R$^{11}$—R$^9$—R$^{10}$;

$R^5$=—OH, —OAlk, —NH-Alk, NR$^8$—R$^9$—R$^{10}$, —NH(CH$_2$)$_m$—R$^{11}$—R$^9$—R$^{10}$;

$R^6$=H and —COOAlk;

$R^7$=—NR$^8$—R$^9$—R$^{10}$, —NH(CH$_2$)$_m$—R$^{11}$—R$^9$—R$^{10}$;

$R^8$=H and -Alk;

$R^9$=—(CH$_2$CH$_2$O)$_n$CH$_2$CH$_2$—;

$R^{10}$=—OH, —OAlk, —NH$_2$, —NHAlk, —NHAcyl, —NAcyl$_2$, —NR$^{12}$R$^{13}$, —COR$^{14}$, —OCH$_2$COR$^{14}$;

$R^{11}$=—CH$_2$CONR$^8$—, —NHCOO—;

$R^{12}$=H and -Alk;

$R^{13}$=H and -Alk;

$R^{14}$=—OH, —OAlk, —NR$^{12}$R$^{13}$;

wherein:

m=2–12;

n=8–500; and

Alk=an alkyl substituent, obtained by the process mentioned above.

According to a further aspect of the present invention, the use of the above water-soluble mono-PEGylated tetrapyrrole derivatives as photosensitizers in photodynamic therapy is disclosed.

The above, and other objects, features and advantages of the present invention will become apparent from the following description.

DETAILED DESCRIPTION OF PREFERRED EMBODIMENTS

Unless defined otherwise, all technical and scientific terms used herein have the same meaning as is commonly understood by one of ordinary skill in the art to which this invention belongs.

Tetrapyrroles are macrocyclic compounds with bridges of one carbon atom, joining four pyrrole units or their modified derivatives. There are many different classes of tetrapyrroles including those containing dihydropyrrole units. As used herein, the term tetrapyrrole refers to pheophorbides, bacteriopheophorbides, chlorins, bacteriochlorins and their derivatives suitable for photodynamic therapy (PDT) and pharmaceutical preparations.

As used herein, PEG refers to a polyethylene glycol chain. A mono-PEGylated tetrapyrrole derivative of the present invention is a compound containing a polyethylene glycol chain, and is obtained by the reaction of a tetrapyrrole with an aminopolyethylene glycol containing a functionalized terminal fragment (FTF) (11–13). This aminopolyethylene glycol is known as a PEGamine derivative.

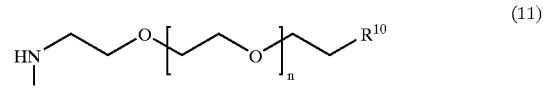

(11)

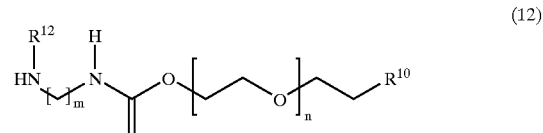

(12)

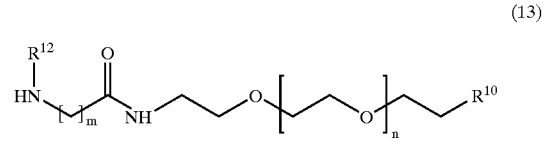

(13)

Wherein:

$R^{10}$=—OH, —OAlk, —NH$_2$, —NHAlk, —NHAcyl, —NAcyl$_2$, —NR$^{12}$R$^{13}$, —COR$^{14}$, —OCH$_2$COR$^{14}$;

$R^{12}$=H and -Alk;

$R^{13}$=H and -Alk;

$R^{14}$=—OH, —OAlk, —NR$^{12}$R$^{13}$;

m=2–12;

n=8–500; and

Alk=an alkyl substituent.

Preparation of the products that are the subject of the present invention is performed by the coupling of PEGamine derivatives of type (11)–(13) with a respective parent tetrapyrrole. For this purpose, traditional methods for attaching organic primary and secondary amines to compounds bearing free or activated carboxy-group(s) can be used, as well as any other convenient methods for the formation of the amide bond. In cases when the parent tetrapyrrole is a pheophorbide derivative, attachment of the amine (11)–(13) via the opening of the cyclopentanone ring can be also used, as is exemplified in the Examples 3 and 6.

The aminopolyethylene glycol (11)–(13) used herein may contain one parent OH group present in parent polyethylene glycols or other functionalized terminal fragments (FTF, $R^{10}$), located at the end of aminopolyethylene glycol chain. Preferred FTFs are selected from the group, comprising OAlk, NH$_2$, NAlk$_2$, COOH, OCH$_2$COOH, NHAcyl, NAcyl$_2$ (including phthalimido, maleido and other cyclic imido-groups). OAlk is preferably OMe.

In the cases when $R^{10}$ is the group that can be reactive in the conditions used to perform the coupling of tetrapyrrole with aminopolyethylene glycol, appropriate selectively modified analogues of compound (11)–(13) are chosen that can carry temporary blocking groups in the $R^{10}$ part to prevent tetrapyrrole units from coupling together. Particularly, the use of diamines of type (11)–(13) ($R^{10}$=NH$_2$) needs the use of the excess of diamine to avoid the attachment of two tetrapyrrole units to diamine. This is not convenient because of the difficulties during chromatography separation of the excess of diamine from the target product of its conjugation with tetrapyrrole. Therefore, in the cases when $R^{10}$ contains primary or secondary amino groups, the use of temporary N-substituted derivatives with tertbutyloxycarbonyl, benzyloxycarbonyl, trichloroacetyl and other appropriate temporary N-blocking groups is preferential.

Similarly, the preparation of the compounds of the present invention from the PEGamine derivatives (11)–(13) bearing the carboxy group in the substituent $R^{10}$, could be performed with the use of derivatives (11)–(13) bearing a free carboxy group, a carboxy group in the state of salt, or a temporarily protected carboxy group in the state of alkyl ester such as methyl, ethyl, tert-butyl and others used traditionally to protect carboxy function.

Mono-PEGylated compounds of the present invention are not only highly water-soluble, they also have good solubility in typical organic solvents. This makes possible their reliable purification with column and other types of chromatography and analysis with HPLC and TLC. Preferred organic solvents for chromatography of the products of the present invention include chlorinated hydrocarbons, ethers, esters, acetonitrile, toluene, acetone, alcohols and their combinations, traditionally used for purification and analysis of organic compounds, particularly of pharmaceutical products.

Presence of the appropriate FTF attached to the polyethylene glycol chain permits further chemical modifications, including an easy conjugation via the respective FTF with labels, carriers, proteins, molecular vectors and other molecules. Particularly, Example 6 describes the synthesis of a water-soluble mono-PEGylated ester compound and its further transformation into its respective acid derivative by saponification.

The present invention also provides the use of water-soluble mono-PEGylated tetrapyrrole derivatives produced according to the present invention in photodynamic therapy (PDT) of cancer and other hyperproliferative diseases and infections. PDT is accomplished by incorporating the derivatives into a pharmaceutically acceptable vehicle for delivery to a specific treatment site. In one embodiment, especially for treatment of skin cancer and other dermatological diseases, the vehicle can be in a form of a cream, gel or, in certain cases, an aerosol liquid dispersant. After delivering the derivatives in the vehicle to a treatment area, sufficient time is given to allow the tetrapyrrole derivatives to preferentially accumulate in the diseased tissue. Finally the treatment area is irradiated with light of a sufficient power and of a specific wavelength to activate the tetrapyrrole derivatives to necrotize the cells of the diseased tissue. Determinations of dark toxicity (described in Example 7) and phototoxicity (described in Example 8) showed excellent properties of the compounds of the present invention for use in PDT.

The present invention is further illustrated by the following examples, but is not limited thereby. The following examples are included for illustrative purposes only and are not intended to limit the scope of the invention. All obtained compounds have correct MS-spectra (CI-MS) and are homogeneously purified according to reversed phase HPLC.

EXAMPLE 1

Preparation of Bacteriopheophorbide a (14)

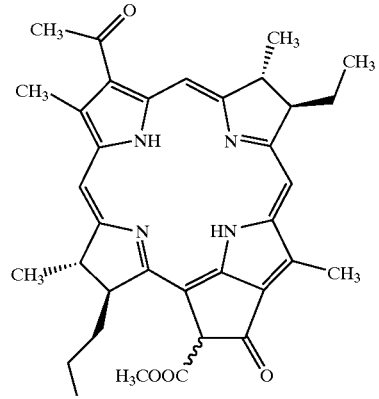

(14)

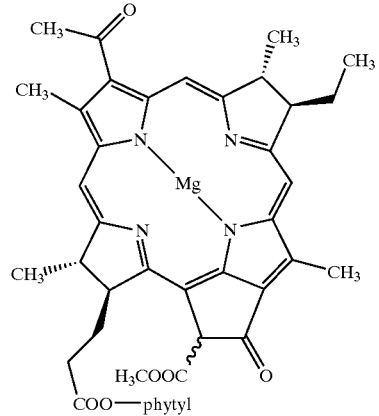

(15)

A solution of bacteriochlorophyll a (15) (45 mg, 0.05 mmol, a product of Sigma-Aldrich Corp.) in a mixture of trifluoroacetic acid (1.2 mL) and water (0.3 mL) was kept at room temperature for 3 hours, concentrated in vacuum (~20 mmHg) at room temperature, diluted with water and extracted with dichloromethane. The extracts were washed with water, dried, concentrated, and purified on Silica gel with a mixture of 5% MeOH—CHCl$_3$ to give 31 mg (98%) of bacteriopheophorbide a (14).

EXAMPLE 2

Preparation of Pyro-Bacteriopheophorbide a (16)

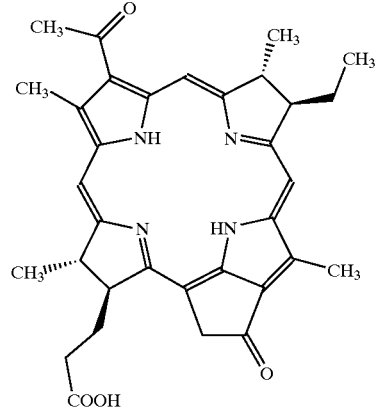

(16)

A mixture of bacteriopheophorbide a (14) (65 mg, 0.11 mmol) and pyridine (4 mL) was refluxed for 12 hrs, cooled, evaporated to dryness, diluted with water and extracted with dichloromethane. The extracts were washed with 1N hydrochloric acid, water, dried, concentrated, and purified on Silica gel with a mixture of 5% MeOH—CHCl$_3$ to give 59 mg (94%) of pyro-bacteriopheophorbide a (16).

EXAMPLE 3

Preparation of Water-Soluble Mono-PEGylated Chlorin e6 Derivatives (17 and 18)

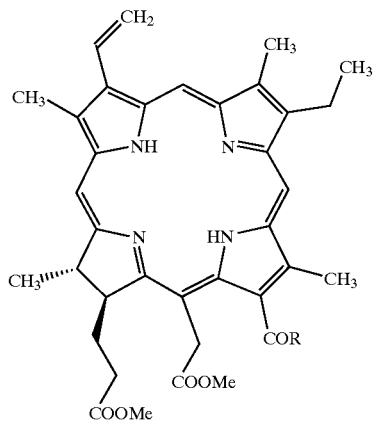

(17) R = NH—PEG$_{750}$—OMe
(18) R = NH—PEG$_{2000}$—OMe

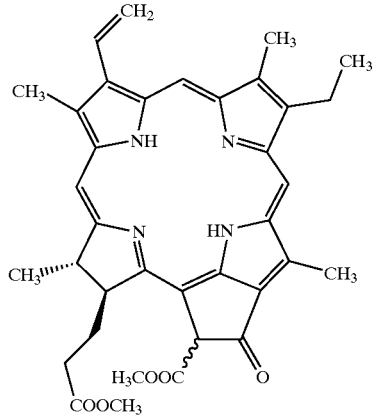

(19)

A mixture of methyl pheophorbide a (19) (10 mg, 0.017 mmol) and MeO-PEG$_{750}$-NH$_2$ or MeO-PEG$_{2000}$-NH$_2$ (0.068 mmol, 4 eq.) (a product of RAPP Polymere GmbH) in tetrahydrofuran (0.5 mL) was kept at room temperature for 3 days, diluted with dichloromethane, washed with 0.5 N HCl aqueous solution, water, dried, concentrated, and purified on Silica gel with a mixture of 5% MeOH—CHCl$_3$. The resulting solution of (17) or (18) was evaporated to dryness, re-dissolved in water (2 mL), filtered through a 45 μm filter and freeze dried to give 60–70% of water-soluble compound (17) and (18), respectively.

EXAMPLE 4

General Procedure for Preparation of Water-Soluble Mono-PEGylated Meso-Pyro-Pheophorbide a Derivatives (20)–(25), Pheophorbide a (26) and (27), Bacteriopheophorbide a (28) and Pyro-Bacteriopheophorbide a (29)

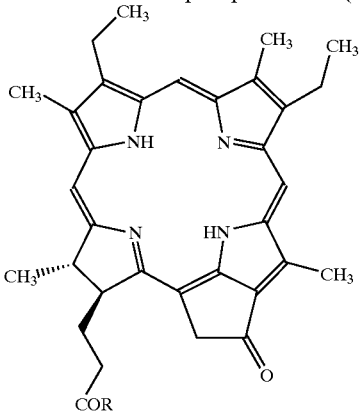

(20) R = NH—PEG$_{750}$—Ome
(21) R = NH—PEG$_{2000}$—Ome
(22) R = NH—PEG$_{5000}$—Ome
(23) R = NH—PEG$_{10000}$—Ome
(24) R = NH—PEG$_{20000}$—Ome
(25) R = NH—PEG$_{300}$—OCH$_2$COOH
(30) R = OH
(31) R = pentafluorophenyloxy

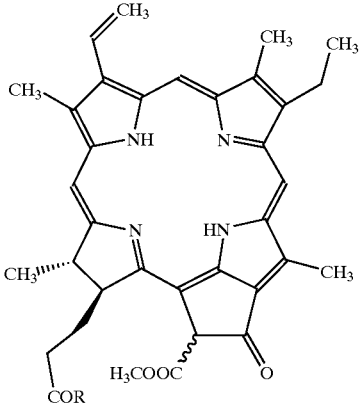

(26) R = NH—PEG$_{750}$—OMe
(27) R = NH—PEG$_{2000}$—OMe
(32) R = pentafluorophenyloxy

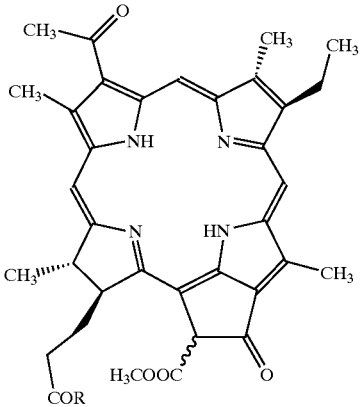

(28) R = NH—PEG$_{2000}$—OMe
(33) R = pentafluorophenyloxy

-continued

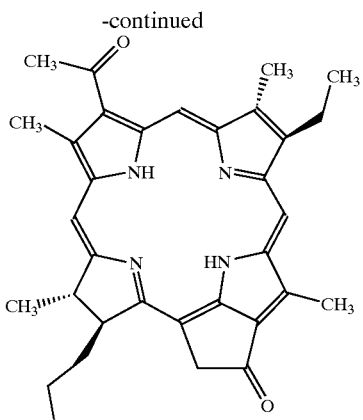

(29) R = NH—PEG$_{2000}$—OMe
(34) R = pentafluorophenyloxy

Meso-pyro-Pheophorbide a (30), pheophorbide a (5), bacteriopheophorbide a (14) or pyro-bacteriopheophorbide (16) (0.03 mmol) is dissolved in dichloromethane (2 mL), then 0.05 mL of triethylamine is added followed by addition of 0.01 mL (0.058 mmol, 1.9 eq.) of pentafluorophenyl trifluoroacetate. The mixture was stirred at room temperature for 10 minutes to produce compound (31), (32), (33), or (34), respectively, diluted with dichloromethane, washed with water, dried, and the resulting solution was added to a solution of appropriate MeO-PEG-NH$_2$, with MW 750, 2,000, 5,000, 10,000, or 20,000 (products of RAPP Polymere GmbH), or HOOCCH$_2$O-PEG$_{3000}$-NH$_2$ (0.039 mmol, 1.5 eq., (product of GlycoSense AG) in dichloromethane (1.0 mL). The mixture was stirred for 0.5–10 hours at room temperature, diluted with dichloromethane, and then washed with 0.5 N HCl aqueous solution. The mixture was then washed with water, dried, concentrated, and purified on Silica gel with a mixture of 5% MeOH—CHCl$_3$. The resulting solution of the corresponding PEG-amide was evaporated to dryness, re-dissolved in water (2–5 mL), filtered through a 45 μm filter and freeze dried to give pure water-soluble compound (20)–(29) in total yields of 70–99%.

EXAMPLE 5

Preparation of Water-Soluble Mono-PEGylated Meso-Pyro-Pheophorbide a Derivatives (35) Bearing Heptamethylenediamino Spacer between Tetrapyrrole and PEG$_{2000}$ Parts

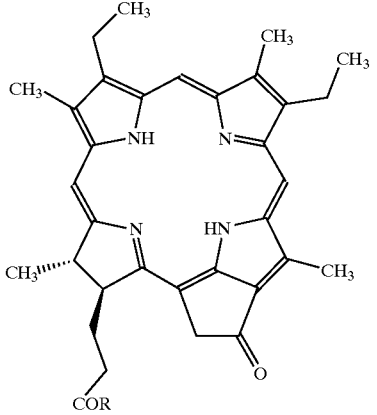

(35) R = NH—(CH$_2$)$_7$NHCOO—PEG$_{2000}$—OMe 1,1'-carbonyldiimidazol (25 mg, 0.15 mmol, 3 eq.) was added to a solution of MeO-PEG$_{2000}$-OH (100 mg, 0.05 mmol, (product of RAPP Polymere GmbH) in tetrahydrofuran (2.0 mL) N. After 10 minutes at room temperature a solution of 1,7-diaminoheptane (33 mg, 0.25 mmol, 5 eq.) in tetrahydrofuran (1.0 mL) was added. The mixture was kept at room temperature for 30 minutes and the product was precipitated by the addition of ether. The latter product was dissolved in dichloromethane (2 mL) and the resulting solution was added to a solution of (31) [prepared from 15 mg (0.026 mmol) of meso-pyro-pheophorbide a (30) as described in the Example 6] in dichloromethane (2 mL). The mixture was kept at room temperature for 30 minutes, diluted with dichloromethane, and washed with 0.5 N HCl aqueous solution. The mixture was then washed with water, dried, concentrated, and purified on Silica gel with a mixture of 5% MeOH—CHCl$_3$. The resulting solution of (35) was evaporated to dryness, re-dissolved in water (2.0 mL), filtered through a 45 μm filter and freeze dried to give 60 mg (85%) of water-soluble compound (35).

EXAMPLE 6

Preparation of Water-Soluble Mono-PEGylated Chlorine e6 Derivatives (36) and (37)

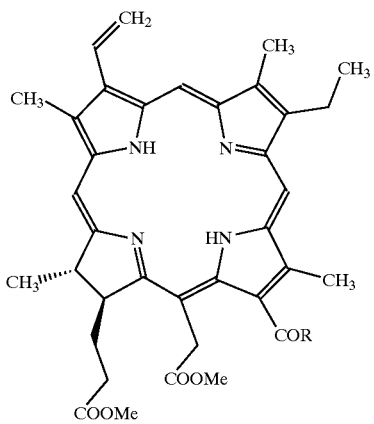

(36) R = NH—PEG$_{3000}$—OCH$_2$COOMe
(37) R = NH—PEG$_{3000}$—OCH$_2$COOH

A mixture of methyl pheophorbide a (20) (10 mg, 0.017 mmol) and MeOOCCH$_2$O-PEG$_{3000}$-NH$_2$ (215 mg, 0.068 mmol, 4 eq.) (product of GlycoSense AG) in tetrahydrofuran (0.5 mL) was kept at room temperature for 3 days, diluted with dichloromethane, washed with 0.5 N HCl aqueous solution, then washed with water, dried, concentrated, and purified on Silica gel with a mixture of 5% MeOH—CHCl$_3$. The resulting solution of (36) was evaporated to dryness, then dissolved in dioxane (2 mL), and 6N sodium hydroxide aqueous solution (0.01 mL) was added and the reaction mixture was refluxed for 10 min. The mixture was then cooled, diluted with dichloromethane, washed with 0.5 N HCl aqueous solution, washed with water, dried, concentrated to dryness, re-dissolved in water (2 mL), and then filtered through a 45 μm filter and freeze dried to give 42 mg (70%) of water-soluble compound (37).

EXAMPLE 7

Determination of Dark Toxicity (Cytotoxicity) of Water-Soluble Mono-PEGylated Pheophorbide a (35) and Water-Soluble Salt of Pheophorbide a (5) with N-methyl-D-glucamine in HeLa Cells To determine dark toxicity of the water-soluble derivative (35) and water-soluble salt of pheophorbide a (5) with N-methyl-D-glucamine (prepared according to U.S. application Ser. No. 10/151,764) in HeLa (human cervix carcinoma cells), cell monolayer cultures were incubated in 96-well plates (seeding density: 7,000 cells per well in Dulbeco-modified essentional medium (DMEM) with 10% fetal calf serum) with increasing concentrations of photosensitizer in the range of 2 to 500 μg/mL and incubated for 48 hours.

The cells were washed with pure DMEM and treated with 10% formalin for 15 minutes at room temperature. The cells were twice washed with water, incubated for 15 minutes with 0.1% solution of crystal violet (50 μl/well), then washed with water and treated with ethanol (100 μl/well). Optical densities of ethanol solutions formed were determined with Specord 100 (Analytik Jena AG, Germany) spectrophotometer at 594 nm to monitor cell survival.

Values are expressed as percentages of non-incubated controls. For each incubation concentration eight experiments were performed. Data from the experiments are given in Table 1, which shows the $IC_{50}$ and $IC_{80}$ values.

TABLE 1

Dark toxicity (cytotoxicity) data for water-soluble PEGylated pheophorbide a (35) and water-soluble salt of pheophorbide a (5) with N-methyl-D-glucamine in HeLa cells (Example 7)

| Photosensitizer | $IC_{50}$ (μg/mL) | $IC_{80}$ (μg/mL) |
| --- | --- | --- |
| salt of pheophorbide a (5) with N-methyl-D-glucamine | 20 | 100 |
| (35) | 500 | 800 |

EXAMPLE 8

Determination of Phototoxicity of Water-Soluble Mono-PEGylated Pheophorbide a Derivative (35) and Water-Soluble Salt of Pheophorbide a (5) with N-methyl-D-glucamine in HeLa Cells Under Irradiation at 662 nm To determine phototoxicity, the water-soluble derivative (35) or water-soluble salt of pheophorbide a (5) with N-methyl-D-glucamine (prepared according to U.S. application Ser. No. 10/151,764) and HeLa (human cervix carcinoma cells) cell monolayer cultures were incubated in 96-well plates (seeding density: 30,000 cells per well in DMEM with 10% fetal bovine serum) with increasing concentrations of photosensitizer ranging from 0.01 to 40 μg/mL. Illumination was performed at 662 nm (Ceralas PDT laser, BioLitec AG, Germany; 150 mW/cm$^2$, 5–20 J/cm$^2$) after a 30-minute incubation period. Cell survival was measured using the MTT assay. Values are expressed as percentages of illuminated, but non-incubated controls. Experiments were performed in octuplets. Data from the experiments are given in Table 2, which shows $IC_{50}$ and $IC_{90}$ values observed after 10 J/cm$^2$ irradiation.

TABLE 2

Phototoxicity data for water-soluble PEGylated pheophorbide a (35) and water-soluble salt of pheophorbide a (5) with N-methyl-D-glucamine in HeLa cells (Example 8)

| Photosensitizer | $IC_{50}$ (μg/mL) | $IC_{90}$ (μg/mL) |
| --- | --- | --- |
| salt of pheophorbide a (5) with N-methyl-D-glucamine | 8.0 | 22.0 |
| (35) | 0.12 | 0.25 |

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A water-soluble mono-PEGylated tetrapyrrole derivative selected from the group consisting of formula 1, 2, and 3:

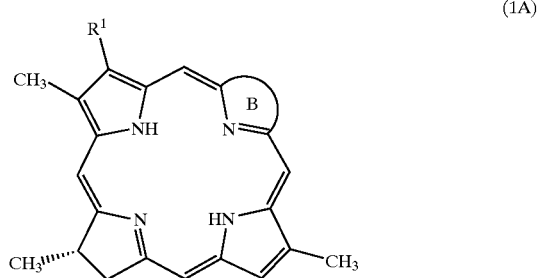

(1A)

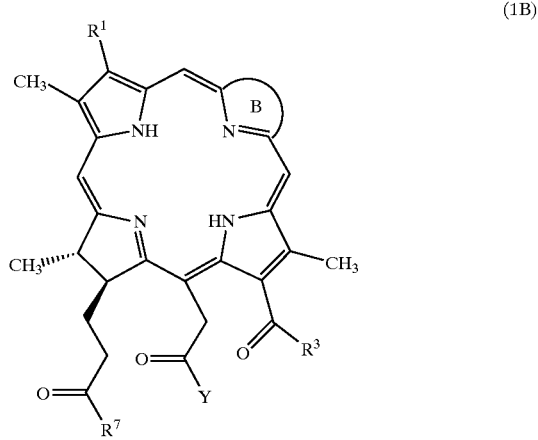

(1B)

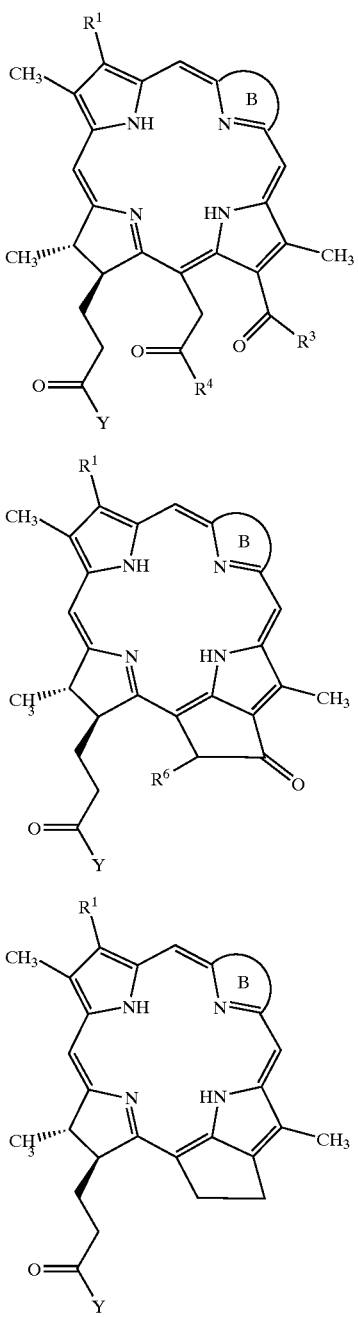

wherein Y is a residue of a functionalized aminopolyethylene glycol H—Y, wherein Y is selected from the group consisting of:

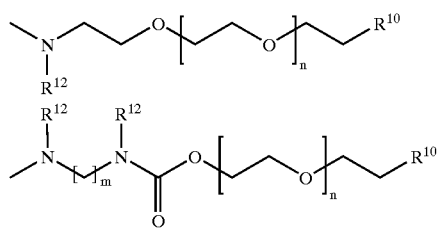

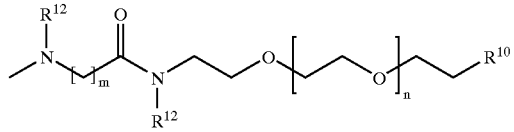

wherein B is a ring having the structure:

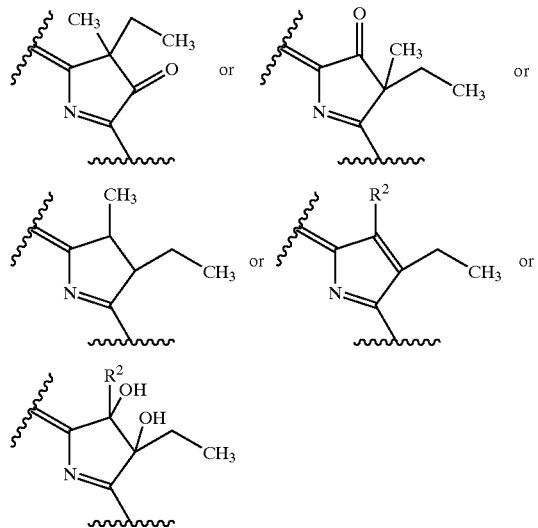

wherein:

$R^1$ = —CH=CH$_2$, —CH(OAlk)CH$_3$, —CHO, —C(O)CH$_3$, —CH$_2$CH$_3$, —CH(Alk)CH(COAlk)$_2$, —CH$_2$CH(COAlk)$_2$, —CH(Alk)CH$_2$COAlk, —CH(Alk)CH$_2$CH(OH)CH$_3$, and —CH$_2$CH$_2$CH(OH)CH$_3$;

$R^2$ = —CH$_3$, —CHO, —CH(OH)Alk, —CH=CHAlk, —CH$_2$OH, and —CH$_2$OAlk;

$R^3$ = —OH, —OAlk, —NH-Alk;

$R^4$ = —OH, —OAlk, —NH-Alk;

$R^5$ = —OH, —OAlk, —NH-Alk;

$R^6$ = H and —COOAlk;

$R^8$ = H and -Alk;

$R^{10}$ = —OH, —OAlk, —NH$_2$, —NHAlk, —NHAcyl, —NAcyl$_2$, —NR$^{12}$R$^{13}$, —COR$^{14}$, —OCH$_2$COR$^{14}$;

$R^{11}$ = —CH$_2$CONR$^8$—, —NHCOO—;

$R^{12}$ = H and -Alk;

$R^{13}$ = H and -Alk; and $R^{14}$ = —OH, —OAlk, —NR$^{12}$R$^{13}$;

Wherein:

m=2–12;

n=8–500; and

Alk=an alkyl substituent.

2. A process for making the water-soluble mono-PEGylated tetrapyrrole derivatives of claim 1, comprising the step of reacting with said functionalized aminopolyethylene glycol H—Y wherein said tetrapyrrole is selected from the group consisting of formula 7, 8, 9, and 10:

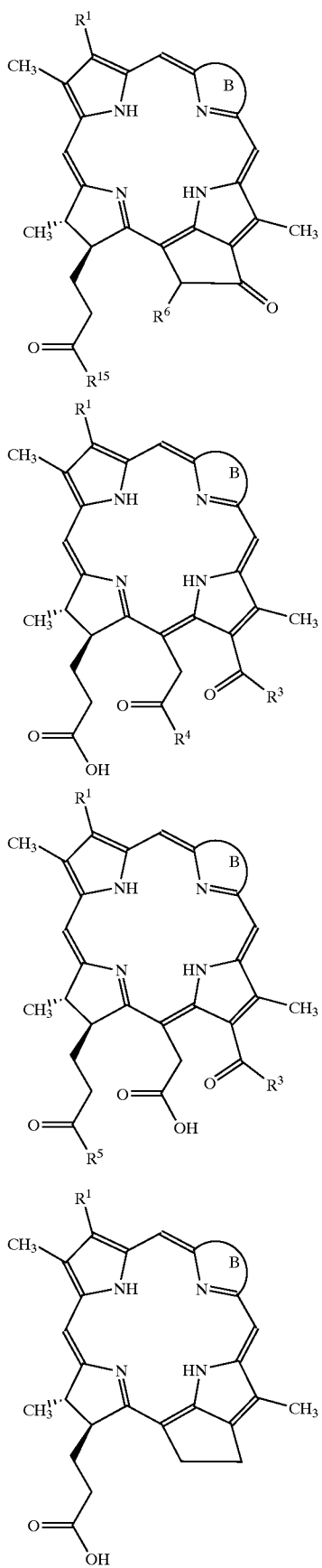

(7)

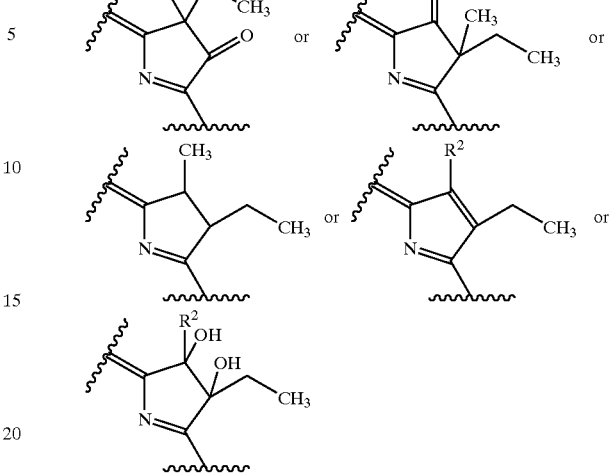

Wherein B is a ring having the structure:

(8)

Wherein:
$R^1$=—CH=CH$_2$, —CH(OAlk)CH$_3$, —CHO, —C(O)CH$_3$, —CH$_2$CH$_3$,
—CH(Alk)CH(COAlk)$_2$, —CH$_2$CH(COAlk)$_2$, —CH(Alk)CH$_2$COAlk,
—CH(Alk)CH$_2$CH(OH)CH$_3$, and —CH$_2$CH$_2$CH(OH)CH$_3$;
$R^2$=—CH$_3$, —CHO, —CH(OH)Alk, —CH=CHAlk, —CH$_2$OH, and —CH$_2$OAlk;
$R^3$=—OH, —OAlk, —NH-Alk;
$R^4$=—OH, —OAlk, —NH-Alk;
$R^5$=—OH, —OAlk, —NH-Alk;
$R^6$=H and —COOAlk;
$R^{15}$=—OH, —NH(CH$_2$)$_m$—R$^{16}$;
$R^{16}$=—COOH, —NH$_2$; and Wherein:
m=2–12; and
Alk=an alkyl substituent.
Alk=an alkyl substituent.

3. The process according to claim 2, wherein said residue of said functionalized aminopolyethylene glycol H—Y, Y, is selected from the group consisting of:

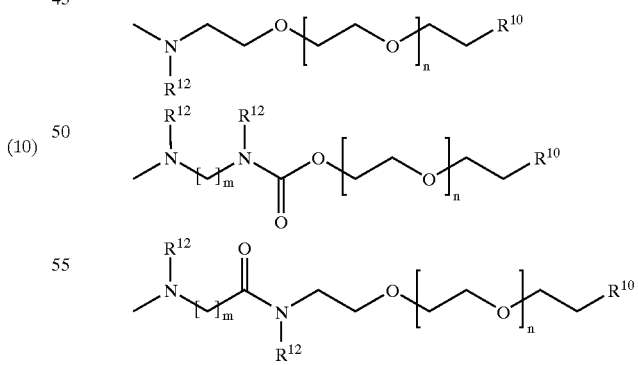

Wherein
$R^{10}$=—OH, —OAlk, —NH$_2$, —NHAlk, —NHAcyl, —NAcyl$_2$, —NR$^2$R$_{13}$, —COR$^{14}$, —OCH$_2$COR$^{14}$;
$R^{11}$=—CH$_2$CONR$^8$—, —NHCOO—;
$R^{12}$=H and -Alk;
$R^{13}$=H and -Alk; and
$R^{14}$=—OH, —OAlk, —NR$^{12}$R$^{13}$;

Wherein:

m=2–12;

n=8–500; and

Alk = an alkyl substituent.

4. The process according to claim 3, wherein OAlk is OMe.

5. The process according to claim 2, wherein said functionalized aminopolyethylene glycol H—Y has a molecular weight of 500–30,000.

6. A process of photodynamic theraphy comprising the steps of: formulating the water-soluble mono-PEGamine tetrapyrrole derivative of claim 1 into a pharmaceutically acceptable vehicle for delivery to diseased tissues at a specific treatment site;

delivering said mono-PEGamine tetrapyrrole-vehicle formulation to said specific treatment site;

allowing said mono-PEGamine tetrapyrrole-vehicle formulation to preferentially accumulate in said diseased tissues;

irradiating said treatment site with light of a sufficient power and wavelength to activate said mono-PEGamine tetrapyrrole.

7. A composition or pharmaceutical preparation comprised of said mono-PEGylated tetrapyrrole of claim 1 as a water solution.

* * * * *